(12) United States Patent
Ohashi et al.

(10) Patent No.: US 10,533,170 B2
(45) Date of Patent: *Jan. 14, 2020

(54) METHOD FOR MANIPULATING MAGNETIC PARTICLES AND DEVICE FOR MANIPULATING MAGNETIC PARTICLES

(71) Applicant: SHIMADZU CORPORATION, Nakagyo-Ku, Kyoto-Shi, Kyoto (JP)

(72) Inventors: Tetsuo Ohashi, Kyoto (JP); Yukio Oikawa, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 94 days.

This patent is subject to a terminal disclaimer.

(21) Appl. No.: 15/125,501

(22) PCT Filed: Mar. 14, 2014

(86) PCT No.: PCT/JP2014/056905
§ 371 (c)(1),
(2) Date: Sep. 12, 2016

(87) PCT Pub. No.: WO2015/136689
PCT Pub. Date: Sep. 17, 2015

(65) Prior Publication Data
US 2017/0073667 A1 Mar. 16, 2017

(51) Int. Cl.
*B03C 1/01* (2006.01)
*B03C 1/033* (2006.01)
(Continued)

(52) U.S. Cl.
CPC .......... *C12N 15/1013* (2013.01); *B01L 3/502* (2013.01); *B01L 3/50273* (2013.01);
(Continued)

(58) Field of Classification Search
CPC ......... B03C 1/00; B03C 1/12; B03C 2201/18; B03C 2201/26; B03C 1/01; B03C 1/0332;
(Continued)

(56) References Cited

U.S. PATENT DOCUMENTS 6,509,193 B1  1/2003 Tajima
2009/0311733 A1  12/2009 Korpeta et al.
(Continued)

FOREIGN PATENT DOCUMENTS

JP  2009-517067  4/2009
JP  2009-186356  8/2009
(Continued)

OTHER PUBLICATIONS

PCT/JP2014/056905, International Search Report dated Jun. 24, 2014, 2 pages—Japanese, 2 pages—English.

*Primary Examiner* — Claire A Norris
(74) *Attorney, Agent, or Firm* — Andrew F. Young, Esq.; Lackenbach Siegel, LLP

(57) ABSTRACT

A magnetic particle manipulation method for magnetic particle comprises the steps of; subjecting magnetic particles and a magnetic solid having a larger particle diameter than said magnetic particles to existing together in a liquid layer, and moving said magnetic solid and said magnetic particles in said liquid layer by a magnetic field manipulation. According to one aspect of the present invention; a manipulation method for magnetic particles comprising the steps of; moving magnetic particles in a first liquid layer into a gelled medium layer by a magnetic field manipulation in a device, wherein gelled medium layers and liquid layers are in-place alternately in a container, moving said magnetic particles present in the gelled medium into a second liquid layer by
(Continued)

the magnetic field manipulation; and moving said magnetic particles along with said magnetic solid in the second liquid layer.

6 Claims, 3 Drawing Sheets

(51) Int. Cl.
    *B01L 3/00*     (2006.01)
    *C12N 15/10*     (2006.01)
    *B03C 1/28*     (2006.01)
    *B03C 1/30*     (2006.01)
    *C12Q 1/6806*     (2018.01)
    *G01N 35/00*     (2006.01)

(52) U.S. Cl.
    CPC .............. *B03C 1/01* (2013.01); *B03C 1/0332* (2013.01); *B03C 1/0335* (2013.01); *B03C 1/288* (2013.01); *B03C 1/30* (2013.01); *B01L 2200/0631* (2013.01); *B01L 2200/0668* (2013.01); *B01L 2200/0673* (2013.01); *B01L 2300/0838* (2013.01); *B01L 2400/043* (2013.01); *B03C 2201/18* (2013.01); *B03C 2201/26* (2013.01); *C12Q 1/6806* (2013.01); *G01N 35/0098* (2013.01); *G01N 2035/00346* (2013.01); *G01N 2035/00534* (2013.01); *G01N 2035/00574* (2013.01)

(58) Field of Classification Search
    CPC ......... B03C 1/0335; B03C 1/288; B03C 1/30; C12N 15/1013; B01L 3/50273; B01L 3/502
    USPC .................................................. 210/222, 695
    See application file for complete search history.

(56) References Cited

U.S. PATENT DOCUMENTS

2012/0329124 A1   12/2012   Tajima
2013/0273552 A1   10/2013   Ohashi
2017/0067923 A1*   3/2017   Ohashi .................. B01L 3/5025

FOREIGN PATENT DOCUMENTS

| | | |
|---|---|---|
| JP | 2010-123984 | 6/2010 |
| WO | WO 97/44671 | 11/1997 |
| WO | WO 2011/059076 | 5/2011 |
| WO | WO 2012/086243 | 6/2012 |

\* cited by examiner

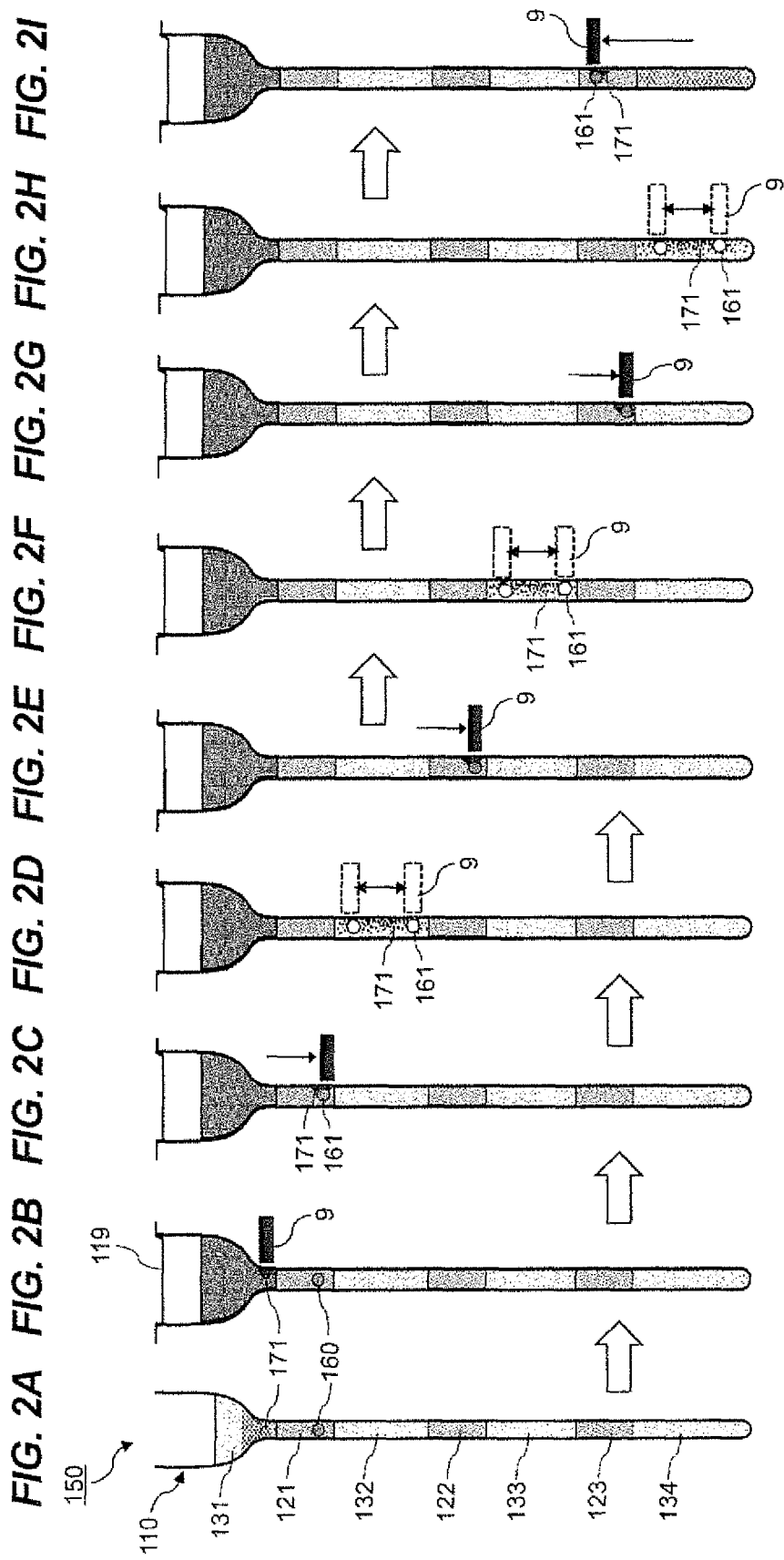

METHOD FOR MANIPULATING MAGNETIC PARTICLES AND DEVICE FOR MANIPULATING MAGNETIC PARTICLES

CROSS REFERENCE TO RELATED APPLICATIONS

This application relates to and claims priority from SN PCT/JP2014/056905 filed Mar. 14, 2014, the entire contents of which are incorporated herein by reference.

FIGURE FOR PUBLICATION

FIG. 1A-1E

BACKGROUND OF THE INVENTION

Field of the Invention

The present invention relates to a manipulation method of a magnetic particle so as to conduct chemical processes including a separation, an extraction, a purification and a chemical reaction of a target substance and further relates to a device for a magnetic particle manipulation applied thereto.

Description of the Related Art

Relative to a medical examination, food safety and hygienic control and monitoring of environment reservation and so forth, a target substance to be detected or subject to a chemical reaction must be extracted from the sample containing a variety of foreign materials. For example, such medical examination may have to conduct detection, identification and quantification of nucleic acids, proteins, saccharides, lipids, bacteria, viruses and radio-active substances and so forth included in the biological samples, e.g., blood, serum, cells, urine and feces and so forth, separated and obtained from plants and animals. In such examination, separation and purification of the target substance may be needed to eliminate a mal-effect relative to the background and so forth due to the foreign materials.

A method of separation and purification of the target substance in the sample using magnetic particles capable of specifically adsorbing the target substance has been developed and commercialized. Relative to such separation and purification using magnetic particles, firstly, the target substance is adsorbed on the surface of the magnetic particles having a particle diameter of approximately several μm and then after the foreign materials attached to the particle surface are washed away, the target substance is desorbed from the particle surface. For example, firstly nucleic acids are liberated from cells in blood when nucleic acids are extracted from blood. At this time, proteins in the cells are denatured using a strong protein denaturant such as a guanidium salt and so forth. The nucleic acids freed from the cells are specifically adsorbed on the silica coated magnetic particles. Following, the foreign materials and so forth attached on the magnetic particles are washed away with a cleaning solution and at last, the nucleic acids are eluted from the magnetic particles.

According to the separation and purification processes using such magnetic particles, a step of separating and recovering the magnetic particles in the liquid phase from the liquid phase by the magnetic manipulation and a step of dispersing the recovered magnetic particles in the liquid phase of the cleaning solution or the elution (liberation) and so forth are repeatedly conducted. Dispersion of the magnetic particles in the liquid phase is generally conducted by vibration and stirring by pipetting or vibrating with e.g., a Vortex mixer. The magnetic particles per se can be separated from the liquid phase by a magnetic manipulation using e.g., magnet so that a process of separation of solid and liquid by e.g., centrifugation can be eliminated and can facilitate to automatize such processes.

For example, a full automation device for a series of operations relative to separation and purification from adsorbing the target substance of the sample on the magnetic particles to cleaning and eluting thereof by conducting both recovery of the magnetic particles from the liquid phase and dispersion of the magnetic particles in the liquid phase by pipetting has been disclosed (e.g., Patent Document 1.) In addition, the Patent Document 2 discloses a method of suppressing a coagulation of the magnetic particles with a repulsive force of zeta potential under the condition in which an electric conductivity coefficient of the supernatant of the dispersion solution of the magnetic particles is not larger than 300 μS/cm.

As a method of separation and purification of the target substance using magnetic particles, the method using move of the magnetic particles in the device, in which liquids such as a cell lysis solution, a washing solution, an elution and so forth and an oil phase of oils and so forth are alternatively layered, is proposed. According to such method, the separation and purification of the target substance in a complete closed system can be conducted while suppressing any contamination. In addition, while continuously keeping such closed condition following the separation and purification, an operation of such as an analytical process can be conducted in the same device.

For example, the Patent Document 3 disclose that the gelled medium as the oil phase can be used relative to the device for the separation and purification, in which the aqueous phase and the oil phase are alternatively layered. According to such method, the magnetic particles in the aqueous phase moves to the inside of the layer of the gelled medium by a magnetic manipulation. Since the gelled has a thixotropic property, the magnetic particles can move inside of the gelled medium layer without damaging the gelled medium layer. On the other hand, the aqueous liquid attached to the magnetic particles cannot move into the inside of the layer of the gelled medium layer. Accordingly, due to a gellation of the oil phase, the magnetic particles adsorbing the target substance moving in the inside of the gelled medium layer can bring the solid-liquid separation (B/F separation) in reality and the separation and purification and recovery of the target substance can be conducted very efficiently.

PRIOR ART RELATED ART DOCUMENTS

Patent Documents

Patent Document 1: WO1997/44671 A
Patent Document 2: JP Patent Published 2010-123984
Patent Document 3: WO2012/086243 A

ASPECTS AND SUMMARY OF THE INVENTION

Problems to be Solved by the Invention

Relative to the separation and purification of the target substance using magnetic particles, each magnetic particle per se draws each other to easily coagulate because recovery and move of magnetic particles in the liquid take place due to manipulation of the magnetic field. When magnetic particles coagulate, the foreign materials incorporate inside the coagulant (in-between particles) cannot be washed away and as results, a defect, in which e.g., the purification of the target substance may become insufficient or the recovery rate thereof may worsen, and may take place. It is important that the magnetic particles coagulated during washing and elution should be dispersed sufficiently in the washing solution or the elution, accordingly.

Particularly, when nucleic acids are extracted from blood, a large amount of the proteins denatured with the denaturant such as guanidium salt and so forth present in the sample so that the magnetic particles per se can adhere each other. Accordingly, such coagulated magnetic particles are too hard to be re-dispersed so that the purity and the recovery rate of the target substance can worsen because removal of foreign materials and elution of nucleic acids are impaired thereby.

In the case of pipetting according to the Patent Document 1, an excess amount of the agent is needed to suppress the coagulation of the magnetic particles and disperse the coagulated particles in the solution. Further, the proteins must be processed with a high concentration of denaturant, e.g., a guanidium salt and so forth, to lyse the cells so that keeping the condition of low electric conductivity as proposed by the Patent Document 2 can be unrealistic.

Further, according to the inventors' studies relative to the Patent Document 3, in which a gel is used for separation, once the magnetic particles coagulate, it is found that the re-dispersion of the magnetic particles in the liquid or the gel was difficult. Accordingly, as well as the above Patent Document 1, the foreign materials enclosed in the coagulant of the magnetic particles and the liquid containing the foreign materials cannot be removed despite the separation process using the gel so that the purity and the recovery rate of the target substance may worsen due to improper washing or defect elution.

Considering the above, a purpose of the present invention is to provide a manipulation method of magnetic particles, by which the magnetic particles can be efficiently dispersed in the solution and the chemical processes including such as separation, extraction, purification and reaction can be very efficiently conducted.

Means for Solving the Problem

Considering the above, according to the present inventors' studies, it was found that the magnetic particles can disperse in the solution along with the move of the magnetic solid to improve the washing effect therefor and the recovery rate thereof by manipulation of the magnetic field under co-existing of the magnetic particles and the magnetic solid having a larger diameter than the magnetic particle can be improved and the present invention was completed, accordingly.

Specifically, the present invention relates to a manipulation method of magnetic particles, wherein the magnetic particles and magnetic solid having a larger particle diameter than magnetic particles coexist in the liquid layer and the magnetic particles move along with the magnetic solid in the liquid layer by the magnetic field manipulation.

According to one aspect of the Embodiment of the present invention, the manipulation of the magnetic particles is conducted in a device in which the gelled medium layer and the liquid layer are alternately installed in a container. According to such aspect; the magnetic particles in the first liquid layer move into the gelled medium by the magnetic field manipulation, the magnetic particles inside the gelled medium layer move into the second liquid layer, and the magnetic particles move along with the magnetic solid in the second liquid layer.

According to the present invention, the step of moving the magnetic particles in the liquid layer is conducted under coexisting with the magnetic solid having a larger diameter than the magnetic particles in the liquid layer. The magnetic particles can be dispersed in the liquid layer, accordingly. Therefore, the magnetic particles can be easily dispersed in the liquid layer, e.g., a washing solution and an elution and so forth, even under the condition in which the magnetic particles per se easily adhere and coagulate each other, so that efficiencies of washing and elution can be improved. Specifically, if the liquid constituting the liquid layer is a washing solution, the magnetic particles can be dispersed in the washing solution even while keeping the target substance being fixed on the magnetic particles to improve the washing efficiency. In addition, if the liquid constituting the liquid layer is an elution, the recovery rate of the target substance can be improved. According to the preferred aspect of the present invention, the magnetic particles move back-and-forth along with the magnetic solid in the liquid layer.

According to the present invention, the particle diameter of the magnetic particles is preferentially at least 50 μm. In addition, the particle diameter of the magnetic solid is at least 10 times larger than the particle diameter of the magnetic particles. As such magnetic solid, a metal having a coating layer on the surface thereof to prevent corrosion in the liquid layer can be applied. It is particularly preferable that if a device or a kit having the magnetic solid preliminarily filling the gelled medium layer or the liquid layer is provided, the metal surface of e.g., iron or stainless steel is processed with coating to prevent corrosion.

The magnetic particles are preferably particles capable of fixing selectively a specific substance. The specific substance that can be selectively fixed on the magnetic particles may include biological substances e.g., nucleic acids, proteins, saccharides, lipids, antibodies, ligands, cells and so forth. In addition, the "biological substances" is not necessary only to be obtained from the in-vivo specimen and may include the substance obtained from the in-vitro specimen (e.g., nucleic acids amplified by PCR and so forth.)

According to one aspect of the Embodiment of the present invention, the manipulation of the magnetic particles is conducted in a device in which at least 2 gelled medium layers and at least 3 liquid layers are included in a container, and at least 1 liquid layer of the liquid layers in the device comprises a different composition from the composition of other layers. According to the present aspect, a plurality of chemical processes (e.g., separation, extraction, purification, reaction and so forth) can be conducted in one device. For example, the magnetic particles adsorbing the target substance such as nucleic acids and so forth move in the wash layer, the gelled medium layer and then the elution in order within the device in which the wash and the elution partitioned by the gelled medium layer are in-place, and the target substance can be freed and recovered in the elution following washing and purification of the target substance in the wash, accordingly.

Further, the present invention relates to a device preferably applicable to the above magnetic particles manipulation. According to the device of the present invention, a gelled medium layer and a liquid layer are in-place alternately and in addition, magnetic particles and magnetic solid having a larger particle diameter than that of the magnetic particles, which move in a container, are included therein.

Further, the present invention relates to a kit to make the above device. According to the present invention, the kit to make the device includes liquid, a gelled medium, magnetic particles and magnetic solid having a larger particle diameter than that of the magnetic particles. Such kit may be the kit in which a part of the configuration elements is preliminarily filled in the predetermined container.

Effect of the Invention

According to the method of the present invention, move of magnetic particles is conducted by magnetic field manipulation under coexisting with the magnetic solid having a larger diameter than that of the magnetic particles in the liquid. This time, the magnet solid moves along with the magnetic particles and accordingly, generated micro-vibration of the magnetic solid thereby decomposes the aggregate of the magnetic particles, which are dispersed in the solution thereby. Accordingly, if the present invention is applied to separation and purification of the target substance such as nucleic acids and so forth, washing efficiency (purity) and recovery yield of the target substance can be improved.

Further, according to the method of the present invention, the magnetic particles move in the gelled medium layer so that the separation between solid and liquid can be conducted. Therefore, comparing to the method of using pipetting to conduct separation between solid, i.e., magnetic particles, and liquid, i.e., an agent e.g., washing, elution and so forth, the method according to the present invention can efficiently separate and recover the target substance with a relatively small amount of the magnetic particles and the agents and as results, an amount of waste solution can be significantly reduced.

The above and other aspects, features and advantages of the present invention will become apparent from the following description read in conjunction with the accompanying drawings, in which like reference numerals designate the same elements.

BRIEF DESCRIPTION OF THE DRAWINGS

FIGS. 2A-2I are illustrating the schematic each process of separation and purification according to the aspect of the Embodiment.

DETAILED DESCRIPTION OF THE PREFERRED EMBODIMENTS

Figures 1A, 1B, 1C, 1D, 1E:
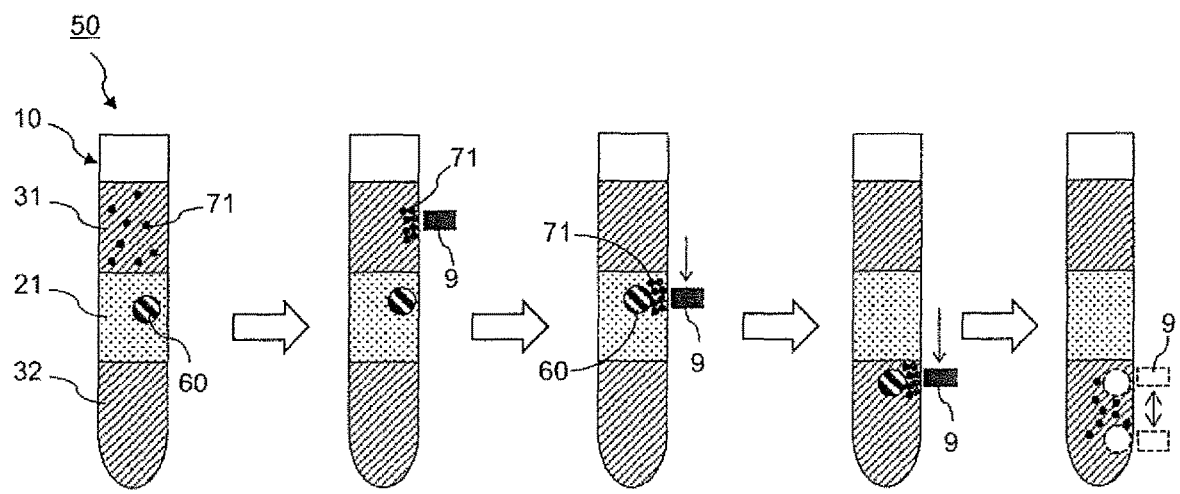
FIGS. 1A-1E are illustrating the schematic summary of a manipulation method of magnetic particles.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

First, the inventor sets forth the summary and the principal of a manipulation method of magnetic particles. FIGS. 1A-1E are a schematic diagram illustrating one aspect of the device 50 being used in the manipulation of the magnetic particles and the method of the manipulation of particles using such device of the present invention. According to the device for particles manipulation of the present invention, the gelled medium layer and the liquid layer are alternately in-place in a container. Referring to FIG. 1A, the inside of the container 10 is filled with a second liquid layer 32, a gelled medium layer 21 and a first liquid layer 31 in order from the bottom thereof. The inside of the medium layer 21 is filled with magnetic solid 60.

It is preferred that the gelled medium configuring the gelled medium layer 21 is not miscible with the liquid layer 31, 32 adjacent thereto, or insoluble or poorly soluble in the liquid layer. For example, when the liquid layer 31, 32 comprises an aqueous solution, the gelled medium layer 21 comprises preferably an oily gelled which is insoluble or poorly soluble in such aqueous solution. In addition, the gelled medium layer is preferably formed from a chemically inert substance. Here, insoluble or poorly soluble in the solution means that a solubility of the solute in the solution is not more than approximately 100 ppm at 25° C. The chemically inert substance is the substance that has no effect to the liquid layer, the magnetic particles and the substance fixed on the magnetic particles, during contacting to the liquid layer or manipulation of the magnetic particles (i.e., process for move of the magnetic particles in the gelled medium.)

The first liquid layer 31 includes the magnetic particles 71. Such magnetic particles 71 can be the magnetic particle on which a specific target substance such as nucleic acids and so forth is fixed thereon. Fixation of the target substance on the magnetic particles 71 can be, for example, conducted in the first liquid layer 31. The magnetic particles 71 preliminarily fixing the target substance on the surface thereof can be added to the first liquid layer 31. Further, the liquid containing the magnetic particle 71 fixing the target substance on the surface thereof can be injected on the gelled medium layer 21 from the opening of the container 10, in which the second liquid layer 32 and the gelled medium layer 21 are filled.

The magnet particles 71 are drawn to the inside wall of the container by the action of the magnetic field. Relative of manipulation of the magnetic field, a permanent magnet (e.g., ferrite magnet and neodymium magnet) or electric magnet and so forth can be applied as a magnet force source. The magnetic particles 71 drawn to the inside wall of the container form aggregates and the liquid configuring the first liquid layer 31 may be incorporated into the aggregates of the magnetic particles. In addition, if the foreign materials other than the target substance are included in the first liquid layer 31, the foreign materials may be incorporated into the aggregates of the magnetic particles. Particularly, denatures proteins and so forth forces magnetic particles so as to adhere each other and accordingly, such foreign materials are also incorporated into the magnetic particles.

When the magnet 9 moves from the side of the first liquid layer 31 of the side of the gelled medium layer 21, the magnet particles 71 move into the first liquid layer 31 to the inside of the gelled medium layer 21. At this time, the most aqueous liquid adhering physically to the surrounding of the magnetic particles 71 as a liquid droplet remain in the liquid portion of the liquid layer 31 detaching from the particles' surface when the magnetic particles 71 move in the inside from the surface of the gelled medium layer 21. On the other hand, the magnetic particles 71 can move easily inside the gelled medium layer 21 while holding the target substance fixed to the particles.

Although the gelled medium can be perforated by that the magnetic particles 71 move into the gelled medium layer 21 or move, the gels can self-restore. When the magnetic particles move in the gels and the shearing force is added by the magnetic manipulation, the gels can be locally fluidized (becoming viscous.) Accordingly, the magnetic particles can easily move inside the gels while perforating the fluidized portion. After the magnetic particles passed, the gels are released from the shearing force so that the gels can be restored in the original elastic status. Accordingly, no perforated hole remains formed in the passed portion so that almost no liquid can move into the gels through the perforated hole of the magnetic particles.

The restoring force due to the thixotropy of the above gels acts as squeezing the liquid along with the magnetic particles 71 out. Accordingly, the magnetic particles 71 become aggregates and even if the magnetic particles incorporating the liquid droplets move into the gelled medium layer 21, the magnetic particles and the liquid droplet can be separated. On the other hand, foreign materials such as denatured protein incorporated in the aggregation of magnetic particles can be hardly removed from the magnetic particles by restoring force of the gels because such foreign materials strongly adhere the magnetic particles each other. Accordingly, such foreign materials move in the gelled medium layer while being incorporated in the aggregate of the magnetic particles per se.

When the magnet 9 moves from the side of the first liquid layer 31 of the side of the gelled medium layer 21, the magnet particles 71 move from the first liquid layer 31 to the inside of the gelled medium layer 21 and magnetic solid 60 is drawn to the magnet 9 mounted inside the gelled medium layer 21 (FIG. 1C.) Accordingly, the magnet solid 60 moves unitarily together with the aggregate of the magnetic particles 71 in the gelled medium layer.

The magnet particles 71 and the magnet solid 60 passed through the gelled medium layer 21 move from the gelled medium layer 21 to the second liquid layer 32 by magnetic field manipulation (FIG. 1D) As describe above, no throughhole is formed in the portion through which the magnetic particles and the magnetic soil passed so that almost no liquid flow from the first liquid layer 31 to the second liquid layer 32 takes place.

When the magnet 9 is moved along the side of the second liquid layer 32, the magnetic solid 60 and the magnetic particles 71 also move into the second liquid layer along with the move of the magnet 9. At this time, the magnetic particles 71 forming the aggregate are dispersed in the second liquid layer (FIG. 1E.) Accordingly to the manipulation method of the magnetic particles of the present invention, the magnetic particles and the magnetic solid are being together in the liquid layer and the magnetic particles move together with the magnetic solid by the magnetic manipulation so that the magnetic particles forming the aggregate can be dispersed in the liquid layer.

Accordingly, if the second liquid layer 32 is a wash, the foreign materials such as denatured proteins and so forth attached to the magnetic particles can be washed out. If the second liquid layer 32 is an elution, the target substance such as nuclei acids and so forth attached to the particles under the condition in which the magnetic particles are dispersed can be eluted (freed) so that the recovery yield of the target substance can be improved. In addition, if the second liquid layer 32 includes the substance that reacts with the target substance fixed to the magnetic particles, the reaction takes place under the condition in which the magnetic particles are dispersed, so that the reaction efficacy can be improved.

The principal dispersion mechanism of the magnetic particles by moving the magnetic particles with the magnetic solid in the liquid layer is not quite clear. As long as a visual observation of the move of the magnetic solid and the magnetic particles, when the magnetic solid 60 moves along the wall of the container 10, it is found that the magnetic solid is slightly vibrating due to friction resistance between the wall of the container and the magnetic solid or along delayed following move of the magnetic relative to the move of the magnet. It is supposed that such slight vibration of the magnetic solid acts so as to disperse the magnetic present in the periphery of the magnetic solid or such slight vibration breaks down the aggregation existing between the wall of the container and the magnetic solid so that the magnetic particles can be quickly dispersed in the liquid layer.

The particle manipulation method of the present invention comprises the step of dispersing the magnetic particles in the liquid layer and can be applied to others not limited to the magnetic particles passed through the magnetic particles. For example, the present invention can be accomplished by that the magnetic field manipulation is conducted under coexisting with the magnetic solid by adding the aggregated magnetic particles from the opening of the container into the liquid layer.

Relative to the magnetic particles passed through the gelled medium, when the particle manipulation method of the present invention is conducted, dispersion can be accomplished in the liquid layer while keeping the closed system. Specifically, referring to FIGS. 1A-1E, FIGS. 2A-2I, the liquid layer, 32, 132, 133, 134 are being held in between the gelled media or between the gelled medium layer and the container so that no access from outside can be allowed while keeping such closed system. If such dispersion of the magnetic particles in the liquid layer is conducted by the pipetting process, the tip of the pipette must be inserted into the liquid layer passing through the gelled medium layer so that the closed system cannot be being kept. In contrast, according to the method of the present invention, the magnetic particles can be dispersed in the liquid layer while keeping the closed system so that any contamination from outside can be suppressed. Further, as illustrated later comparing the Example and the Comparison Example, the method of the present invention can provide higher dispersion efficiency of the magnet particles than the pipetting process and accordingly, wash and recovery of the target substance can be accomplished highly efficiently.

The magnetic particles 71 applicable in the present invention is capable of being processed including aggregation, dispersion and moving and so forth in liquid or a gelled medium by action of the magnetic field. Such magnets may include a ferromagnetic metal such as iron, cobalt, nickel and so forth and a compound thereof, an oxide thereof and an alloy metal thereof and so forth. Specifically, such magnet can include magnetite ($Fe_3O_4$), hematite ($Fe_2O_3$ or $\alpha Fe_2O_3$), maghemite ($\gamma Fe_2O_3$), titanomagnetite ($xFe_2TiO_4.(1-x)Fe_3O_4$, ilmenohematite ($xFeTiO_3.(1-x)Fe_2O_3$, pyrotite ($Fe1-xS(x=0\sim0.13).Fe_7S_8(x\sim0.13)$)), greigite($Fe_3S_4$), geothite ($\alpha FeOOH$), chromium oxide ($CrO_2$), permalloy, alnico magnet, stainless steel, samarium magnet, neodymium magnet, barium magnet.

From facilitating standpoints to run particle manipulation in the liquid and the gelled medium, the particle diameter of the magnetic particles is preferable in the range of 0.1-20 µm and more preferably in the range of 0.5-10 µm. The shape of the magnetic particles is preferably a homogeneous spheric shape but can be irregular shape and the distribution of the particle diameter can be in some extent as long as the particle manipulation is operable. The composition unit of the magnetic particles can be single substance or can comprise a plurality of substances.

The magnetic particles are preferably capable of specifically fixing a specific target substance. If the fixing method is capable of holding the target substance on the surface of particle or inside particle, such method is not particularly limited and a variety of fixing mechanisms including known physical adhesion, chemical adhesion and so forth can be applied. For example, a variety of interactions including Van der Waals force, hydrogen bonding, hydrophobic interaction, ion-ion interaction, π-π stacking and so forth can fix the target substance on the surface of the particle or inside thereof.

The target substance that can be selectively fixed on the particles may include biological substances e.g., nucleic acids, proteins, saccharides, lipids, antibodies, ligands and cells and so forth. If the target substance is a biological substance, such target substance can be fixed on the particle surface by molecular recognition. For example, if the target substance is a nucleic acid, the nucleic acid can be specifically adhered to the particle surface by using the silica coated magnetic particles. Further, if the target substance is an antibody (e.g., labeled antibody), a receptor, an antigen and a ligand and so forth, such target substance can be selectively fixed on the particle surface by an amino acid group, a carboxyl group, an epoxy group, avidin, biotin, digoxigenin, protein A, protein G and so forth on the particle surface.

Relative to a magnetic particle, the substance adhering e.g., a compound having a variety of functional groups including silica, streptavidin, *Staphylococcus aureus*, protein A, protein G, immunoglobulin and so forth, or being coated with such compound, which specifically fixes the target substance on the surface of the above magnet surface, can be preferably applied. Such magnetic particles can be a commercially available product, e.g., Dynabeads® from Life Technologies and MagExtractor® from Toyobo and so forth.

[Magnetic Solid]

The magnetic solid 60 according to the present invention may include a ferromagnetic metal such as iron, cobalt, nickel and so forth and a compound thereof, an oxide thereof and an alloy metal thereof and so forth as well as illustrated relative to the magnet comprising the above magnetic particles. A shape of the magnetic solid is not particularly limited and can be sphere, polyhedron, and rod and so forth.

The particle diameter of the magnetic solid is preferably larger than that of the magnetic particle. Meantime, if the magnetic solid is non-spheric, the major axis is deemed as the particle diameter thereof. The particle diameter of the magnetic solid is preferably at least 50 µm, more preferably at least 100 µm and most preferably at least 150 µm. Even if the magnetic particles are forming aggregates, the magnetic particles can be dispersed in the liquid by move due to the magnetic manipulation under coexisting with the magnetic solid having a large particle diameter. The particle diameter of the magnetic solid is preferably at least 10 times larger than the particle diameter of the magnetic particle, more preferably at least 30 times larger, and most preferably at least 50 times larger.

The maximum particle diameter of the magnetic solid is not particularly limited as long as movable inside the container. For example, if the container is a tube and the magnetic solid is a sphere, the particle diameter of the magnetic solid should be smaller than the inner diameter of the container. From the view of facilitating the manipulation with magnetic field, the particle diameter of the magnetic solid is preferably smaller than 10 mm, more preferably smaller than 5 mm and most preferably smaller than 3 mm. Further, the particle diameter of the magnetic solid is preferably than 100000 times smaller than the particle diameter of the magnetic particle, more preferably 50000 times smaller, and most preferably 10000 times smaller.

A commercial metal ball such as an iron ball and a stainless steel ball for ball bearing and so forth can be applies as-is to the magnetic solid. In addition, the magnetic solid may have a function. For example, surface of iron or stainless steel can be coated to add corrosion-resistance against a chemical reagent and a sample.

Particularly, when the magnetic solid is exposed to the liquid layer or the gelled medium in the particle manipulation device for a long time, metal such as iron comprising the magnetic solid is corrosive and corrosion material (e.g., metal ion eluted in the liquid layer) may affect to the reaction of reagents and samples (e.g., enzyme reaction or antigen-antibody reaction), a sample fixation and elution. In contrast, the magnetic solid has coating on the metal surface thereof to prevent corrosion so that an affect due to metal corrosion can be suppressed.

If the metal surface is coated to provide corrosion resistance, the coating material is not particularly limited as long as capable of preventing metal corrosion in the gelled medium layer or in the liquid layer and can be an inorganic material such as metal, metal oxides and so forth or a plastic material. Such metal material may include gold, titan and platinum and so forth. Such plastic materials may include a fluorine-based resin such as tetrafluoroethylene and so forth and an epoxy-based resin and so forth. In addition, the coating material can be preferably a material that shall least affect inhibition of reactions with reagents and samples and fixation and elution of the sample.

A method of forming such coating layer on metal surface is not particularly limited. For example, when metal coating with e.g., gold, titan and platinum and so forth to provide corrosion resistance on the metal surface is processed, a plating method or a dry-process (evaporation coating, spatter, CVD and so forth) can be preferable applied. When resin coating is processed on the metal surface, a wet coating can be preferably applied.

If coating to prevent corrosion of metal is peeled off or damaged due to physical impact, the metal is exposed and metal corrosion may take place due to such exposed area. Accordingly, the thickness of coating is preferable in the range of several µm to several hundreds µm. Wet coating is preferred to form the resin layer to provide such thickness of the coating layer. Relative to the resin material, a resin solution and liquid glue can be applied. Relative to the liquid glue, any commercial glue for metal can be applied as-is. For example, a two-pack curing epoxy resin adhesive can be cured at room temperature and is capable of forming easily the coating layer having the above thickness so that it can be preferably applied as coating material to prevent metal corrosion.

When wet coating is applied to dry or cure the resin solution, it is preferred that the drying condition is set under which peel-off of the coating layer. For example, when, after coating, the magnetic solid is subject to stand for drying and cursing, it is preferred that the coating solid should be subject to stand on the material to which the resin material is hardly adhere or the material having solubility resistance to the solvent for coating solution, after coating.

A coating layer other than corrosion resistance coating can be formed on the surface of magnetic solid. For example, the magnetic solid surface can be coated with a variety of functional molecules as the other than the substance to be fixed to the magnetic particles is fixed to the magnetic solid surface. Other than that, the magnetic solid surface can be coated with optical materials such as luminescent materials or fluorescent materials and so forth. According to such configuration, the position of the magnetic solid can be optically detected so that, for example, the configuration can be applied to position detection or position correction of the magnetic solid or the magnetic particles when the particle manipulation is being automated. Further, relative to a micro-flow system, the magnetic solid can be also operable as an actuator for a valve and a pump on the magnetic field manipulation by adjusting quality of material of the magnetic solid, the size and shape thereof Other than that, the magnetic solid can be a receptor of driving power of the flow control element relative to magnetic resonance and can be also utilized as a heat source of a chemical reaction based on heat generation on electromagnetic induction.

According to the aspect of Embodiment 1 referring to FIGS. 1A-1E, a magnetic solid 60 is preliminary installed in the gelled medium layer 21, but the magnetic solid can be preliminary installed in the second liquid layer 32. Further, the magnetic solid can be inserted in the liquid layer 31 or liquid can be injected to the magnetic solid mounted on the gelled medium layer 21. Further, the magnetic solid can be inserted together with the magnetic particles and liquid in the container. In addition, according to the aspect of Embodiment 1 referring to FIGS. 1A-1E, one magnetic solid is applied to one device but alos a plurality of magnetic solids can be applied.

[Container]

According to the present invention, a manipulation of the magnetic particles is conducted in the liquid layer filled in the container 10. A material property and a shape thereof is not particularly limited as long as being capable of moving the magnetic solid in the container and holding liquid and a gelled medium therein. For example, a linear tube structure (capillary tube) having an inner diameter in the range of about 1-2 mm and a length in the range of about 55 mm-200 mm or a structure formed by attaching another plate onto the top of a plate, in which a linear groove having a width in the range of about 1-2 mm, a depth in the range of about 0.5-1 mm and a length in the range of about 50-200 mm is formed, can be applied.

If an extremely small size of container is applied, a micro-device for manipulation of a micro-amount of liquid or a tip for manipulation of a micro-amount of liquid can be provided. Further, the shape of the container is not limited to a tube or a plate and the moving pathway of particles can have a cross structure or a tau structure and so forth. In addition, the container can have a spindle shape container like an Eppendorf tube and so forth.

According to the present invention, the magnetic particles 71 in the container 10 can be movable by the magnetic field manipulation so that the container can be sealed following addition of a sample. If the contained can be sealed, contamination from outside can be prevented. Accordingly, when the manipulation is conducted while fixing the labile substance such as RNA and so forth to the magnetic particles, it is particularly advantageous. When the contained is sealed, the opening of the container can be methodologywise sealed by heating and an appropriate sealing means can be applied to seal. When the particles or aqueous liquid should be taken out of the container following manipulation, it is preferred that the opening should be sealed removably using such as a resin stopper and so forth.

The magnetic particles and the magnetic solid move along the inside wall of the contained by the magnetic field manipulation. Specifically, the inside wall of the container can be a conveying surface for the magnetic particles and the magnetic solid. Accordingly, if the inside wall of the container has a water-repellent property, separation of liquid from the magnetic particles can be accelerated and separation between liquid and solid can be highly efficient. It is preferred that the inside wall of the container has a contact angle of aqueous liquid in the range of about 95°-135° at 25° C.

Materials having such property may include a polyolefin such as polypropylene, polyethylene and so forth, a fluorine-based resin such as tetrafluoroethylene and so forth, a resin material such as polyvinyl chloride, polystyrene, polycarbonate, cyclic polyolefin and so forth. Other than such materials, ceramic, glass, silicone and metal and so forth can be applied. Coating with a fluorine-based resin or silicone can be conducted to increase water-repellent property of the inside wall of the container.

Roughness of the inside wall surface of the container is not particularly limited. The inventor studied and confirmed that the magnetic particles are dispersed efficiently and the target substance can be purified by washing well and recovering in a high yield in both container having a smooth surface with a mathematical average Ra not more than 0.1 μm and container having a rough surface with Ra not less than 1 μm.

During or after particle manipulation, if an optical measurement such as absorbance, fluorescence, chemiluminescence, bioluminescence, refractive index is conducted or an optical irradiation is conducted, a container having optical transparency can be preferably applied. In addition, if the container is optically transparent, it is preferred because the status of particle manipulation in the container can be visually confirmed. On the other hand, if liquid and magnetic particles must be shielded from light, it is preferred that a container such as a metal container having no optical transparency and so forth is preferably employed. According to the purpose of use, a container having an optical transparent part and a non-optical transparent part can be employed.

[Liquid]

Liquid configuring a liquid layer 31, 32 provides the base for the chemical processes including extraction, purification, reaction, separation, detection, analysis and so forth of the target substance fixed on the magnetic particle surface. A type of liquid is not particularly limited, but it is preferred that the liquid does not dissolve the gelled medium. Accordingly, as such liquid, an aqueous solution including water solution, a mixed solution of water and organic solvent and so forth is preferably applied. Not only liquid is just operative as a medium for chemical processes, but also may be directly involved in such chemical processes or may contain a compound involved in such processes as a component thereof. Such being involved substance may include a substance that reacts with a reactive substance fixed to magnetic particles, further reacts with the substance that is fixed on the surface of the magnetic particles by such reaction, a reaction reagent, fluorescent substance, a variety of buffers, surfactants, salts and a variety of other adjutants, and an organic solvent such as alcohol. An aqueous solution can be provided in any forms such as water, water solution and water suspension. When a plurality of liquid layers are filled in the container via gelled medium layer in the container, liquid configuring a liquid layer can be the same or different.

[Gelled Medium]

A gelled medium 21 forming a gelled medium layer should be a gel form or a paste form prior to the particle manipulation. As described before, the gelled medium is preferably insoluble or poorly soluble in liquid layer 31, 32 and a chemically inert substance.

A material or a composition of the gelled medium is not particularly limited. The gelled medium can be formed by gellation, in which a gelling agent is added to an insoluble or poorly soluble substance in water, such as fat oil, ester oil, hydrocarbon oil, silicone oil and so forth. The gel (physical gel) formed by the gelling agent is forming a 3 dimensional network by weak intermolecular bond such as a hydrogen bond, Van der Waals force, hydrophobic interaction, electrostatic attraction force and so forth so that such gel can change reversibly from sol to gel by outside stimulation such as heat and so forth. Such gelling agents to be applied include hydroxy fatty acid, dextrin fatty acid ester, glycerin fatty acid ester and so forth. An application amount of the gelling agent can be appropriately determined considering the physical property of gel in the range of e.g., 0.1-5% by weight based on 100% by weight of insoluble or poorly soluble liquid substance in water.

Gellation method is not particularly limited. For example, heating insoluble or poorly soluble liquid substance in water is heated, adding the gelling agent to the heated liquid substance and then dissolving completely the gelling agent followed by cooling to lower temperature than sol-gel transition temperature can form a physical gel. Heating temperature can be decided appropriately based on physical properties of the liquid substance and the gelling agent.

In addition, hydrogel material (e.g., gelatin, collagen, starch, pectin, hyaluronic acid, chitin, chitosan, alginic acid or a derivative thereof and so forth) that is prepared by being subject to equilibrium swelling in liquid can be applied as a gelled medium. Relative to hydrogel, hydrogel material subject to chemical crosslink, gelling agent (e.g., a salt of alkali metal or alkali earth metal such as lithium, potassium, magnesium and so forth or a salt of transition metal such as titan, gold, silver, platinum and so forth, and further, silica, carbon, alumina and so forth) to provide gel and so forth can be applied.

[Filling Gelled Medium and Liquid]

Filling gelled medium and liquid in the container can be conducted by an appropriate method. When a tube type container is employed, one opened end of the container is sealed prior to filling and preferable gelled medium or aqueous liquid are filled from the other open end in order. When a gelled medium is filled in such a small capillary having an approximate inner diameter in the range of 1-2 mm, for example, the capillary can be filled up by injecting the gelled medium to the predetermined position thereof with the metal needle mounted to a Luer lock syringe.

The amount of the gelled medium and liquid to be filled in the container can be determined appropriately based on the amount of magnetic particles subject to the manipulation and the type of the manipulation and so forth. If a plurality of gelled medium layers or liquid layers are set, the amount of each layer can be the same or different. While the thickness of each layer can be appropriately set, the layer thickness is preferably in the range of e.g., approximately 2 mm-20 mm.

[Device for Particle Manipulation and the Kit for the Same]

Filling the gelled medium and the liquid into the container can be conducted just before the particle manipulation or can be conducted at the adequate time prior to the particle manipulation. As described above, when the gelled medium is insoluble or poorly soluble in the liquid, even if a significant time past after filling, almost no difference takes place in-between relative to the reaction and absorption thereof. The device for the magnetic particle manipulation according to the present invention can be provided as the container is ready filled with the liquid and the gelled medium. Further, the device ready mounted with the magnetic particles and the magnetic solid also can be provided.

The magnetic particles alone or as a dispersion thereof in the liquid can be provided separately from the main body of the device per se. In such event, the magnetic particles can be provided as a configuration member of the kit to build the device.

The magnetic solid can also be provided separately from the main body of the device. The magnetic particles and the magnetic sold together in the liquid can be provided as the configuration members. Meantime, when a device and a kit in the state in which the magnetic solid is filled in the gelled medium or is dispersed in the liquid are provided, the magnetic solid should be exposed to the liquid layer or the gelled medium for a long time depending on the storage condition of the device and the kit. Accordingly, as the purpose to prevent corrosion and deterioration of the magnetic solid, as described above, the magnetic solid having coated metal surface can be preferably applied.

A kit according to the present invention can include the magnetic particles and the magnetic solid as a configuration element of the kit in addition to other configuration members, e.g., the container, the gelled medium, liquid and so forth. Further, the kit can be configured to be capable of filling the liquid and/or the gelled medium additionally according to necessity even more than the state in which the container is filled with the liquid and/or the gelled medium.

The amount of the magnetic particles included in the device or the kit is determined from case by case depending on the applied manipulation type and an amount of each aqueous solution. For example, when a long and thin capillary tube having the inner diameter in the range of approximate 1-2 mm, the amount of the magnetic particles is preferably in the range of approximate 10-200 µg.

[Manipulation of Magnetic Particles]

According to the present invention, the magnetic particles 71 fixing a target substance move from the first liquid layer 31 to the gelled medium layer 21 so that solid-liquid separation (B/F separation) can be conducted. In addition, the magnetic particles in the gelled medium layer 21 moves to the second liquid layer 32 so that the chemical processes including extraction, purification, reaction, preparation, detection, qualitative/quantitative analysis and so forth relative to the target substance can be conducted. Such magnetic particles manipulation can be also applied to a pretreatment prior to a variety of analyses, a preparation (separation) process, a dissolving process, a mixing process, a dilution process, a stirring process, a temperature control process (heating or cooling) and so forth.

The reaction may include biological reactions such as an enzymatic reaction, an immunochemical reaction, which causes a change of biological substance, other than an inorganic reaction and an organic reaction. Such biological reactions may include e.g., reactions of biological substances including nucleic acids, proteins, lipids, saccharides and so forth in the synthesis system, metabolic system and immune system. The target substance subject to a reaction and an analysis is not limited to a chemical substance and a biological substance, if being able to be specifically fixed to the magnetic particles, so that a nuclear substance and a radiochemical substance also can be subject thereto.

[Separation and Purification of Nucleic Acids]

Hereinafter, referring to FIGS. 2A-2I, the inventor illustrates an Embodiment of separation and purification of nucleic acids. Referring to FIG. 2A, relative to the tube device 150, the tube container 110 is filled inside with the nucleic acid extract 131, the first wash solution 132, the second wash solution 133 and the nucleic acid elution 134 along the moving direction of the magnetic particles 171, which has the gelled medium layer 121, 122, 123 in-between each other.

A sample including nucleic acids is not particularly limited, for example, and may include biological samples; such as animal tissues, plant tissues, body fluid, egesta and so forth; and cells, protozoa, fungi and viruses, which contain nucleic acids. Body fluid includes blood, spinal fluid, saliva, milk and so forth and egesta includes feces, urine, sweat and so forth. In addition, any combination of a plurality of the above samples can be included. Cells may include white blood cells and blood disks in blood, denuded cell of mucosa cells of buccal cells and so forth and white blood cells in saliva, and any combination thereof can be applied. The sample containing nucleic acids can be prepared, for example, in the aspect of a cell suspension solution, a homogenate and a mixed solution with cell lysis solution, and so forth.

(Nucleic Acid Extraction Solution)

A nucleic acid extraction solution 131 used to extract nucleic acids may include a buffer solution containing a chaotropic material, a chelating agent such as EDTA and so forth, and tris-hydrogen chloride and so forth. In addition, the nucleic acid extraction solution may contain a surfactant such as Triton X-100 and so forth. The chaotropic material may include guanidine hydrochloride, guanidine isothianic acid, potassium iodine, urea and so forth. A chaotropic salt is a strong protein denaturation agent is operative to lyse cell proteins and free nucleic acid inside cell nuclei into the solution and also suppress an action of nucleic acid degradative enzyme. In addition, nuclear protein binding to nucleic acid is decomposed by a protease such as protease K and so forth so that the purity of nucleic acid and recovery yield can be improved.

In the state of that such substances are present, nucleic acids specifically adsorb to the surface of silica particles (or silica coated particles.) Accordingly, when the above sample containing nucleic acids and silica coated magnetic particles are added to the nucleic acid extraction solution 131, nucleic acids are selectively fixed to the surface of the magnetic particles 71. Any specific method to extract nucleic acids from the sample containing nucleic acids can be determined appropriately. For example, referring to Patent Document JP H2-289596, extraction and purification of nucleic acids from the sample containing nucleic acids using magnetic particles can be performed.

Once the sample containing nucleic acids, nucleic acid extraction solution and magnetic particles are added to the inside of the container 110, it is preferred to prevent any contamination from outside by closing the top of the container 110 with a cover 119 to seal the device.

[Moving of the Magnetic Particles to the Gelled Medium Layer]

After the magnetic particles are well dispersed in the nucleic acid extraction solution followed by fixing the nucleic acids as the target substance to the surface of the magnetic particles, when a magnet 9 is closed to the side of the container containing nucleic acid extraction solution 131, the magnetic particles 171 are drawn to the inside wall of the container in the periphery of the magnet 9 (FIG. 2B.) Denatured proteins and so forth originating from the sample are included in the nucleic acid extraction solution so that the magnetic particles drawn to the magnet can be likely to form aggregates.

Then after, the magnet 9 moves along the side wall of the container so that the magnet particles 71 moves into the gelled medium layer 121. At this time, if a moving rate of the magnet 9 is excessively high, the gel may be physically damaged and the recovery force thereof may be lost. Accordingly, it is preferred that the moving rate of the magnet is in the range of approximately 0.1-5 mm/sec.

When the magnet 9 is getting close to the side of the gelled medium 121, the magnet solid 160 filled in the inside of the gelled medium layer 121 is drawn to the magnet 9. Since, the magnet particles 171 and the magnet solid 160 are unified and move in the gelled medium and further move to the first wash solution 132 (FIG. 2C.)

[Wash Solution]

The first wash solution 132 and the second wash solution 133 is acceptable if components (e.g., proteins, saccharides and so forth) other than nucleic acids included in the sample and the reagents used for processes, e.g., nucleic acid extraction and so forth, are freed into the wash solution while keeping the state in which nucleic acid is fixed to the particle surface. Such wash solutions may include e.g., high concentration aqueous solution of sodium chloride, potassium chloride, ammonium sulfate and so forth, and aqueous alcohol solution of such as ethanol, isopropanol and so forth. A composition of the first wash solution and the second wash solution can be either the same or different.

When the magnet 9 moves along the side of the first wash solution 132, the magnetic particles 171 move together with the magnetic solid 160 and the magnetic particles 171 are dispersed in the wash solution (FIG. 2D) so that wash efficiency of the magnetic particles can be improved. It is preferred that the magnet moves back-and-forth along the side of the wash solution to conduct washing sufficiently. Meantime, the manipulation is conducted under coexisting with the magnetic solid so that the magnetic particles can be dispersed as described above.

Then after, when the magnet 9 moves from the side of the first wash solution 132 of the side of the gelled medium layer 122 (FIG. 2E.) Further, following the magnet 9 moves to the side pf the second wash solution 133, the magnet moves back-and-forth to disperse well the magnetic particles so that washing of the magnetic particles in the second wash solution can be conducted (FIG. 2F.)

Meantime, referring to FIGS. 2A-2I, an example in which the first wash solution 132 and second wash solution 133 are filled in the container 110 through the gelled medium 122 is illustrated, but a number of type of wash solution can be one or more than 3. Further, washing can be skipped as long as no undesired problem relative to purpose of separation and application takes place.

The magnet 9 moves from the side of the second wash solution 133 of the side of the gelled medium layer 123 so that the magnetic particles 171 and the magnetic solid 160 can move into the gelled medium layer 123 (FIG. 2G.) Further, the magnet 9 moves from the side of the nucleic acid eluent 134 so that the magnetic particles 171 and the magnetic solid 160 can move into the nucleic acid eluent 134.

(Nucleic Acid Eluent)

Water or buffer solution containing low concentration salts can be applied as a nucleic acid eluent. Specifically, tris buffer, phosphate buffer, distilled water and so forth can be applied. Above all, 5-20 mM tris buffer having adjusted pH 7-9 is generally applied. The particles fixing nucleic acids move into the nucleic acid eluent so that the nucleic acid can be freed from the particle surface. A specific method to elute the nucleic acid from the particle fixing the nucleic acid is the method of suspending the particles in the above eluent. An elution condition including the suspension method, a stirring time for suspension, temperature on elution and so forth can be appropriately determined so as to increase the recovery yield of the nucleic acids.

When the magnet 9 is moved along the side of the nucleic acid eluent 134, the magnetic particles 171 move together with the magnetic solid 160 and the magnetic particles 171 are dispersed in the nucleic acid eluent (FIG. 2H.) Accordingly, the nucleic acids fixed to the magnetic particles 171 are efficiently desorbed and become free in the nucleic acid eluent so that the recovery yield of the nucleic acids can be improved.

Then after, if desired, referring to FIG. 2I, the magnet 9 is moved along the side of the contained to the side of the gelled medium layer 123 so that the magnetic particles 171 and the magnetic solid 160 can reenter into the gelled medium layer 123. Accordingly, such process, the magnetic particles 171 and the magnetic solid 160 are eliminated from the nucleic acid eluent 134 so that the recovery of the nucleic acid eluent can be facilitated.

The nucleic acids recovered in the nucleic acid eluent can be, if desired, concentrated or dried followed by being subject to an analysis or a reaction and so forth.

The inventor illustrates the separation and purification of nucleic acids using the magnetic particles in the above but the target substance is not limited to the nucleic acids fixed to the magnetic particles and the aspect of the present invention can be applied to a variety of target substance other than nucleic acids. For example, if the surface of magnetic particles coated with molecules specifically capable of fixing an antibody of protein G, protein A and so forth is applied, a magnetic particle manipulation relative to the antibody can be operative.

As an example, when an enzyme-linked immuno-sorbent assay is conducted, the antibody is fixed on the surface of magnetic particles and the magnetic particles and magnetic solid move seriatim by a magnetic manipulation so that an antigen reaction between a first antibody fixed on the surface of the magnetic particles and an antigen being tested (test substance) in the sample; an antigen-antibody reaction between an enzyme-labeled second antibody and the antigen being tested; a chromogenic reaction between the enzyme binding to the second antibody and a coloring substance contained in the aqueous liquid; can be conducted seriatim in each liquid layer partitioned by a gelled layer. The magnetic particles are dispersed together with the magnetic solid in each liquid layer so that the quantification capability of ELISA can be improved.

Accordingly, if the type of liquid filled in the device is changed depending on the type of a target substance and the purpose of a process, the aspect of the present invention can be applied to not only extraction, purification and separation of the target substance but also a variety of reaction, detection, qualitative and quantitative analyses, and so forth.

EXAMPLES

Hereinafter, the inventor illustrates further specifically the present invention comparing an Example relative to the DNA extraction from the human total blood using magnetic beads and a Comparative Example thereof. The invention may not be limited to the following Examples.

Example

Preparation of Tube Manipulation Device

200 μL of eluent 134 (1 mM EDTA, 10 mM tris hydrogen chloride buffer pH8.0); a gelled medium layer 123; 200 μL of a second wash solution 133 (0.5M NaCl, 70% ethanol); a gelled medium 122; 200 μL of a first wash solution 132 (4 mM guanidine hydrogen chloride, 30% ethanol); a gelled medium 121; and a nucleic acid extract solution 131 (4 mM guanidine hydrogen chloride, 5% (w/v) of Triton X-100, 50 mM tris hydrogen chloride buffer, pH7.0) are filled in a polypropylene tube container 110 (inner diameter 1.8 mm) in order from the bottom (refer to FIG. 2A.)

The gelled medium layers 121-123 are filled with the gel (commercial product name KSG-15, Shinetsu Chemical) so as to provide each layer having approximately 1 cm thickness of each layer. A SUS 403 metal ball 160 having particle diameter 1.2 mm thereof is inserted into the gelled medium 121 in the middle of filling the gelled medium layer 121 into the tube container. Further, magnet beads 171 (Silica coated magnetic beads (average particle diameter 3 μm) for nucleic acids extraction) provided with the nucleic acid extraction kit, MagExtractor® Genome, from Toyobo, are re-suspended in distilled water) are added to the nucleic acid extraction solution 131. The applied amount of the magnetic beads 171 is 500 μg.

Accordingly, referring to FIG. 2A, the tube device having 4 aqueous layers 131, 132, 133, 134 and 3 gelled medium layers 121, 122, 123; which are alternately layered; the gelled medium layer 121 including the metal ball 160 as the magnetic solid; and the nucleic acid extract solution 131 having the magnetic beads 171; is prepared.

[DNA Extraction Process]

Human whole blood 50 μL including EDTA as an anti-coagulant is poured into the nucleic acid extract solution 131 from the opening of the tube device. The blood and the magnetic beads are well agitated in the nucleic acid extract solution using a micropipette so that DNA can be freed and adsorbed to the surface of the magnetic beads. Then, the opening of the container 110 is sealed with a cover to seal the container.

Next, a neodymium magnet (column shape of 6 mm diameter and 23 mm length, available from Niroku Sei-sakusyo, Commercial product name "NE127") is closed to the side of the tube device so as to gather the magnet beads 171 fixing DNA in the nucleic acid extract solution 131 to the periphery of the magnet 9. Then, the magnet 9 moves to the side of the gelled medium layer 121 from the side of the nucleic acid extract solution 131 so as to introduce the magnet beads 171 into the gelled medium layer 121. At this time, the metal ball 160 set in the gelled medium layer 121 is also drawn to the magnet 9 together with the magnetic beads 171 (FIG. 2C.)

The magnet 9 moves from the side of the gelled medium layer 121 to the side of the first wash solution 132 so as to move the magnet beads 171 together with the metal ball 160 as-is into the first wash solution. It is visually confirmed that when the magnet moves back-and-forth along the side of the first wash solution 132, the metal ball moves as if following the magnet 9 so that the magnetic beads 171 can be dispersed in the wash solution 132 (FIG. 2D.)

Then, following the same procedure, the magnet 9 moves along the side of the container so that the magnetic beads 171 and the metal ball 160 in the first wash solution 132 can be introduced into the gelled medium layer 122 (FIG. 2E) and further, the magnet moves back-and-force in the second wash solution 133 so that the magnetic beads 171 can be dispersed in the wash solution (FIG. 2F.) Then, the magnet 9 moves along the side of the container so that the magnetic beads 171 and the metal ball 160 can be introduced into the gelled medium layer 123 (FIG. 2G) and further, the magnet moves back-and-force in the nucleic acid eluent 134 so that the magnetic beads 171 can be dispersed in the nucleic acid eluent so as to desorb DNA from the surface of the magnetic beads and be free in the nucleic acid eluent (FIG. 2H.)

At the end, the magnet 9 moves along the side of the container so that the magnetic beads 171, from which DNA has been desorbed, and the metal ball 160 can be reintroduced into the gelled medium layer 123 from the nucleic acid eluent 134 (FIG. 2I.) The periphery of the boundary surface of the polypropylene tube surface between the nucleic acid eluent 134 and the gelled medium layer 123 is snicked with a cutter knife to break the tube and the nucleic acid eluent 134 is recovered from the opening thereby.

Comparative Example 1

As well as the Example 1, the tube device having aqueous layers and gelled medium layers, which are alternately layered, is prepared. However, according to the Comparative Example, no metal ball is inserted in the gelled medium layer 121. The particle manipulation moving the magnet as well as the Example 1 is conducted using such device. According to the Comparative Example 1, as well as the Example 1, the magnet moves back and forth along the side of the wash solution 132, 133 and the nucleic acid eluent 134, but the magnetic beads are as in the aggregation statue and are not dispersed in the liquid layer.

Comparative Example 2

According to the Comparative Example 2, DNA is extracted from whole blood by pipetting process according to the standard protocol based on a nucleic acid extraction kit using magnetic beads (Toyobo, "MagExtractor® Genome" without applying the device having a gelled medium layer.

First, dispense 50 µL of human whole blood into the capacity 1.5 mL of microtube, add 375 µL of the eluent and 20 µL of magnetic beads dispersion solution 20 µL, and agitate vigorously turning Vortex mixer for 10 min so as to free DNA and adsorb DNA on the surface of the magnetic beads. Then, the microtube is set to the magnetic stand and left for approximately 30 seconds to gather the magnetic beads followed by removing the supernatant using a micropipette.

After 450 µL of the first wash solution are poured into the microtube and the magnetic beads are dispersed in the wash solution using the micropipette, the microtube is set to the magnetic stand and left for approximately 30 seconds to gather the magnetic beads followed by removing the supernatant using the micropipette. After the same process is repeated once using the first wash solution, washing by the same process using 450 µL of the second wash solution is repeated twice.

The microbeads following washing are dispersed in the 50 µL of eluent by the micropipette process so as to desorb DNA from the surface of the magnetic beads and then to be freed in the eluent. The microtube is set to the magnetic stand and left for approximately 30 seconds to gather the magnetic beads followed by removing the supernatant using a micropipette.

[Evaluation]

Figure 3:
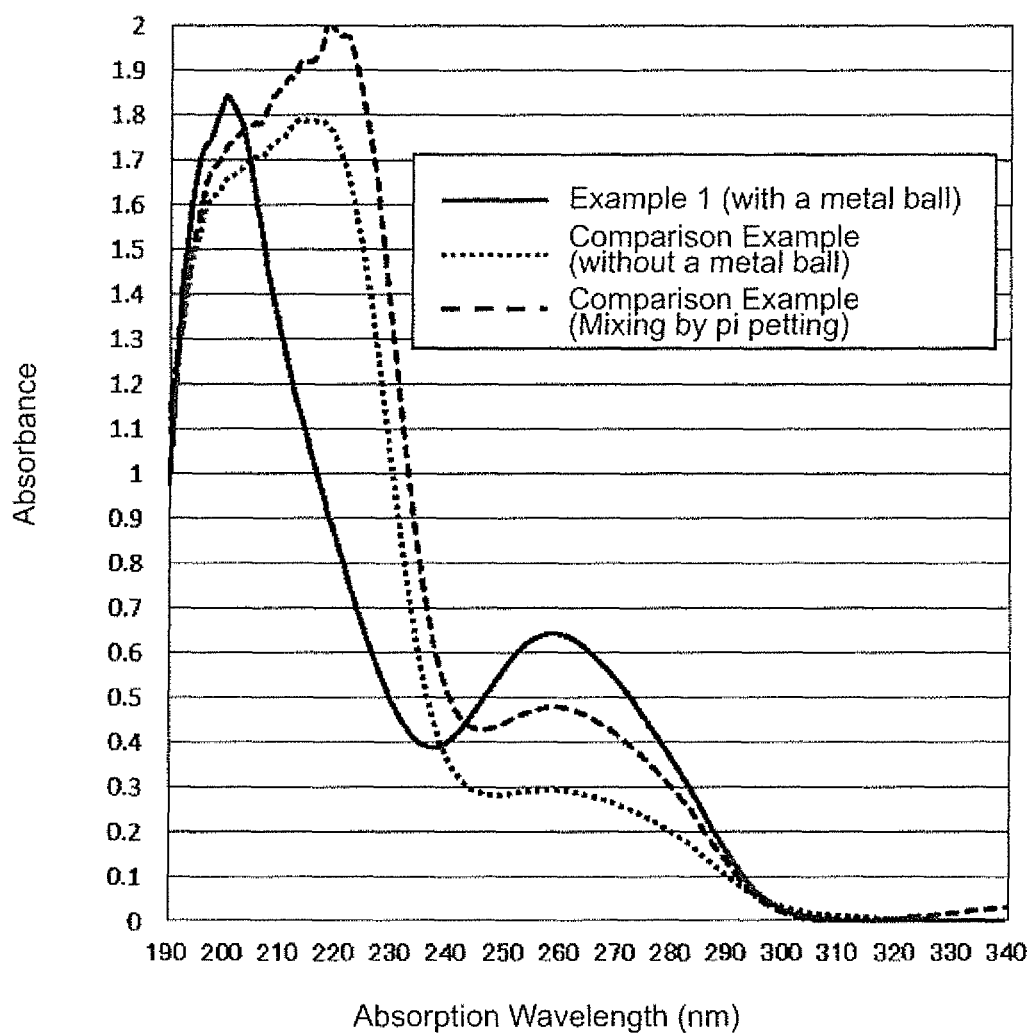
FIG. 3 is each UV absorption spectrum of the nucleic acids extracted and purified using magnetic particles manipulation relative to the Example and the Comparison Example.

UV absorption spectrum of the recovered eluent of each Example and Comparative Example are measured using the spectrophotometer ("BipSpec nano" Shimadzu.) Results are shown in FIG. 3. Further, the absorbance ratios (A260/A280 and A260/A230) at wavelengths 230 nm, 260 nm, 280 nm) are obtained from the UV absorption spectra.

[Table 1]

Relative to UV spectrum of the Example 1, the peak at wavelength 260 nm and the bottom of the peak at 230 nm, which are characteristically subject to DNA, are provided and the absorbance ratio (A260/A230) between 260 nm and 230 nm is approximately 1.3. In addition, since the absorbance ratio between 260 nm and 280 nm, which is a benchmark of purity of DNA, is approximately 1.8, it is understandable that the highly pure DNA is obtained.

In contrast, relative to the Comparative Example 1 and the Comparative Example 2, if the purity of DNA is high, the bottom of the peak appears at around 230 nm, but as the bottom of the peak shifts to around 240 nm, it is understandable that many foreign materials remain. According to the Comparative Example 2 in which the magnetic beads are dispersed by a pipetting process, it is visually observed that the magnetic beads are dispersed in the liquid as well as the Example 1. However, referring to FIG. 3 and Table 1, it is deemed that dispersion and washing of the magnetic beads are insufficient by the pipetting process and therefore the foreign materials remain.

Consequently, even if blood, which tends to easily form aggregated cluster of the magnetic beads, is applied as the sample, according the method of the present invention, the magnetic beads can be more efficiently dispersed than the method using the conventional pipetting process and as results, it is understandable that the target substance, DNA, can be obtained in high purity.

Example 2: Particle Manipulation Using Magnetic Solid Having a Coating Layer

The metal ball made of SUS403 as the magnetic solid according to the Example 1 above is immersed in a nucleic acid extraction buffer (50 µL) containing 2M guanidine hydrogen chloride and corrosion of the surface of the metal ball is visually recognized in a week. According to the Example 1, DNA extraction process is conduced immediately after the magnetic solid is inserted in the tube device so that no concern can takes place even if the metal ball is applied as-is, but it can be concerned that if the metal ball is contacted to a high concentration salt solution and so forth for a long time (e.g., in the case of that the device is stored for a long time prior to practical application after preparation thereof), corrosion of the metal ball ca be concerned. Therefore, according to the Example 2, the magnetic solid having the surface of the metal ball coated with an epoxy adhesion, which is two liquid-components curing type at room temperature, dried and cured for 10 min at room temperature is applied. When the metal ball coated with the epoxy resin layer is immersed in a nucleic acid extraction buffer (50 µL) containing 2M guanidine hydrogen chloride and corrosion of the surface of the metal ball is visually recognized in a week, no change takes place before-and-after being immersed and no corrosion is recognized.

[Preparation of the Tube Device and DNA Extraction Process]

Instead of using as-is the metal ball made of SUS403, having 1.2 mm particle diameter, the metal ball coated with the epoxy resin layer above is applied after being immersed in the nucleic acid extraction buffer containing 2M guanidine hydrogen chloride for a week. Other than that, a tube manipulation device is made as well as the Example 1 above and DNA extraction is conducted by the magnetic field manipulation.

It is confirmed that UV spectrum of the nucleic acid eluent provides a large ratio of A260/A230 as well as the Example 1 and DNA having high purity is obtained. As results, it is understandable that even if a coating layer for preventing corrosion in the liquid layer is formed on the metal surface, fixing DNA to magnetic beads and elution are not disturbed and the target substance can be obtained efficiently in a high purity.

REFERENCE OF SIGN

50 Magnetic particles manipulation device
10 Container
21 Gelled medium layer
31, 32 Liquid layer
60 Magnetic solid
71-73 Magnetic particles
9 Magnet
150 Particle manipulation for nucleic acid extraction
110 Tube-shape container
121-123 gelled medium (Silicone gelled)
131 Liquid layer (nucleic acid extraction solution)
132, 133 Liquid layer (wash)
134 Aqueous liquid (Nucleic acid elution)
160 Magnetic solid (Metal sphere)
171 Magnetic particles (Magnetic beads)

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A magnetic particle manipulation method for magnetic particles, to which a target substance is fixed in a container, the container including a first liquid layer and a second liquid layer and a gelled medium layer between the first liquid layer and the second liquid layer, the method comprising the steps of:
   providing in said first liquid layer said magnetic particles each having a first diameter, and a magnetic solid having a second diameter, said second diameter of said magnetic solid being larger than each first diameter of each said magnetic particle;
   moving said magnetic solid and said magnetic particles from said first liquid layer into said gelled medium layer by moving a magnet along an outer side wall of said container with the magnetic particles aggregated around said magnetic solid;
   moving said magnetic solid and said magnetic particles aggregated around said magnetic solid from said gelled medium layer into said second liquid layer by moving said magnet along said outer wall of said container; and
   dispersing said aggregated magnetic particles into said second liquid layer by moving said magnet back-and-forth along said outer wall of said container at a speed such that said magnetic solid moves back-and-forth in said second liquid layer along an inside wall of said container following said moving of said magnet thereby dispersing said aggregated magnetic particles into said second liquid layer separate from said magnetic solid.

2. The manipulation method for magnetic particles according to claim 1, wherein:
   the particle diameter of said magnetic solid is at least 50 µm.

3. The manipulation method for magnetic particles according to claim 1, wherein:
   the particle diameter of said magnetic solid is at least 10 times larger than the diameter of said magnetic particles.

4. The manipulation method for magnetic particles according to claim 1, wherein:
   said magnetic solid has a coating layer on the metal surface for preventing corrosion in said first or second liquid layer.

5. The manipulation method for magnetic particles according to claim 1, wherein:
   said magnetic particles are capable of selectively fixing at least one target substance selected from the group consisting of nucleic acid, protein, saccharides, lipid, antibody, receptor, antigen, ligand and cell, said method further comprising a step of fixing said target substance to said magnetic particles.

6. The manipulation method for magnetic particles according to claim 5, further comprising at least one of:
   a step of eluting said target substance from said magnetic particles while dispersing said magnetic particles in said second liquid layer, and
   a step of washing said magnetic particles while dispersing said magnetic particles in said second liquid layer, while keeping said target substance fixed to said magnetic particles.

* * * * *